United States Patent [19]

Barnes et al.

[11] Patent Number: 4,911,152
[45] Date of Patent: Mar. 27, 1990

[54] FEMORAL TRACTION SPLINT

[75] Inventors: Scott L. Barnes, Altamonte Springs; Harold J. Haun, Longwood, both of Fla.

[73] Assignee: Aero Products, Inc., Longwood, Fla.

[21] Appl. No.: 866,372

[22] Filed: May 23, 1986

[51] Int. Cl.$^4$ ............................................. A61F 5/04
[52] U.S. Cl. .................................................. 128/84 C
[58] Field of Search ................. 128/84 R, 84 A, 84 B, 128/84 C, 85, 87 R, 87 A, 88, 80 R, 80 F, 75, 86, 93

[56] References Cited

U.S. PATENT DOCUMENTS

| | | | |
|---|---|---|---|
| 780,113 | 1/1905 | Marcum | 248/240.2 |
| 1,573,296 | 2/1926 | Brasell | 128/85 |
| 1,598,931 | 9/1926 | Patche | 248/359 E |
| 2,198,908 | 4/1940 | Ellis | 128/84 R |
| 2,260,216 | 10/1941 | Doyle | 128/85 |
| 2,319,609 | 5/1943 | LaCrosse | 128/84 R |
| 2,384,779 | 9/1945 | Williams | 128/84 R |
| 2,625,727 | 1/1953 | Chappel | 248/359 E |
| 2,791,441 | 5/1957 | Phillips | 248/359 E |
| 3,906,942 | 9/1975 | Lumb, Jr. et al. | 128/84 C |
| 3,942,521 | 3/1976 | Klippel | 128/85 |
| 4,143,653 | 3/1979 | Wichman | 128/87 A |
| 4,265,230 | 5/1981 | Jordon | 128/84 C |
| 4,328,794 | 5/1982 | Holmes | 128/85 |

Primary Examiner—James R. Feyrer
Attorney, Agent, or Firm—James H. Beusse

[57] ABSTRACT

A traction splint for applying traction to an injured limb of a patient. The traction splint includes a pair of spaced adjustably extensible side members, a traction mechanism coupled to first ends of the side members for exerting a pulling force on the limb, and a cross member traversing second ends of the side members and adapted to abut a portion of the patient. The cross member is pivotally connected to the second ends whereby extending one of the side members more than the other side member angularly displaces the cross member with respect to the side member.

2 Claims, 3 Drawing Sheets

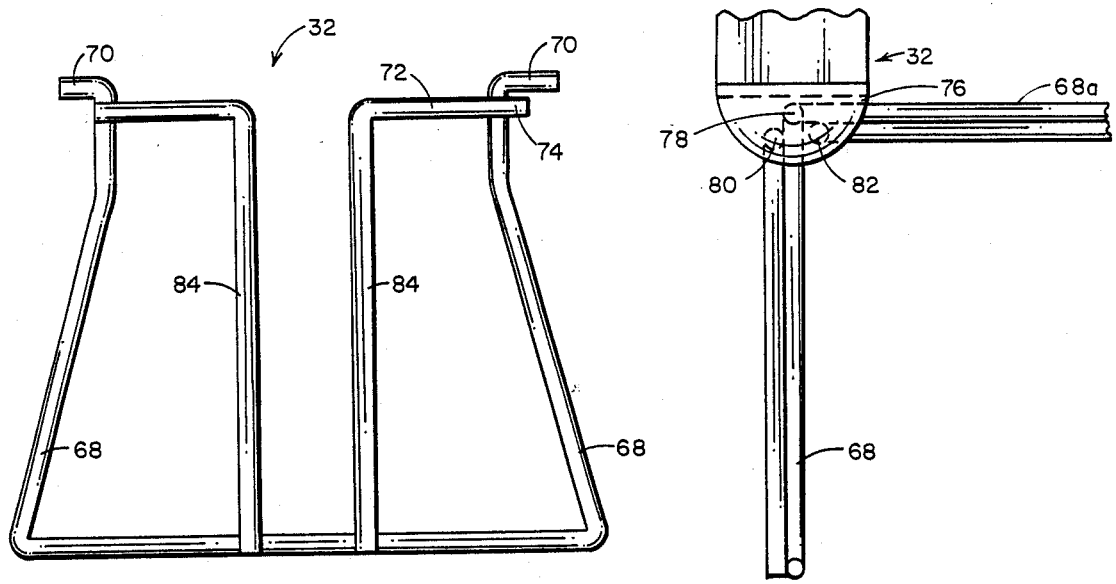
FIG. 4
FIG. 5
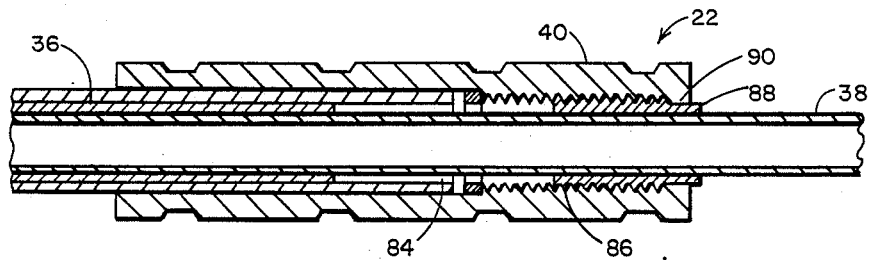
FIG. 6
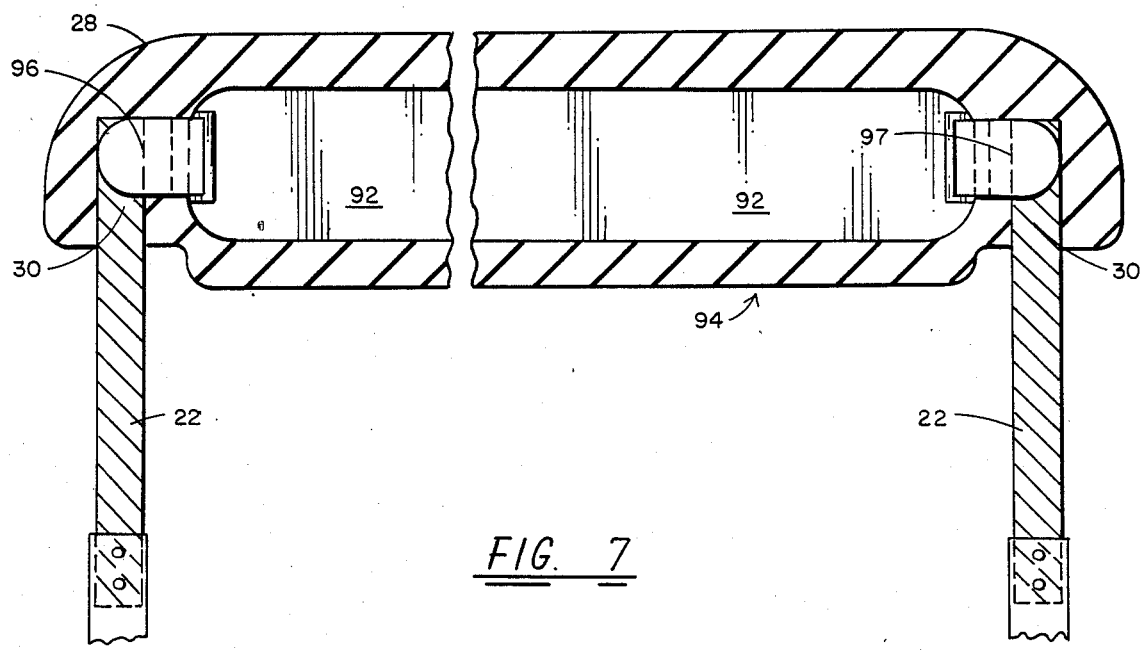
FIG. 7

FEMORAL TRACTION SPLINT

FIELD OF THE INVENTION

This invention relates generally to splints and, more particularly to splints which allow traction to be applied to a lower extremity fracture, specifically the femur or thigh bone.

BACKGROUND OF THE INVENTION

Fractures of arms and legs require appropriate splinting. Generally, splints should be applied at the scene of injury before the patient is moved. Preferably, a slow steady pull is applied to the injured limb to relax the muscles and reduce the chance of injury to adjacent soft tissue. A steady pull along the longitudinal axis of the injured limb brings the fragment which can be controlled into alignment with the fragment which cannot. With the splint properly positioned and the application of tension to the limb, injury caused by subsequent movement of the patient can be minimized.

Prior art splints generally have a take up reel or the like for applying a pulling force, or traction, to the injured limb of a patient. Prior U.S. patents pertaining to traction splints include: U.S. Pat. No. 4,328,794 to Holmes; U.S. Pat. No. 3,477,428 to Hare; and U.S. Pat. No. 3,419,002 to Santosus. The traction splints disclosed in each of these patents include a pair of side members, a padded cross member connected to first ends of the side members and adapted to abut an upper portion of the leg of the patient, and a traction mechanism connected to second ends of the side members. The traction mechanism is adapted of attachment to the ankle of the patent and pulls on the ankle such that traction is applied to the leg between the cross member and the ankle of the patient. It is believed that one disadvantage of such prior art traction splints is that the side members are not independently extensible and, therefore, one of the side members cannot be extended a greater distance than the other side member to angularly displace the cross member with respect to the side members. Accordingly, the cross member must be positioned below the groin of the patient. If a fracture of the femur occurs near the hip of the patient, positioning the cross bar below the groin of the patient may not provide the needed support for the fracture. It is believed another disadvantage of the prior art traction splints is the discomfort and circulation blockage caused by the cross members. Each of the traction splints in the noted patents disclose cross members formed from a circular pipe or tube and covered by a circular pad. The cross members may be arcuate to accommodate the shape of the patient's leg. However, since a circular tube is used, a relatively small portion of the cross member will actually abut a portion of the patient's extremity. I is believed that since the forces from the cross member must be supported by this small portion of the patient, circulation in the affected extremity will be restricted and the patient will experience discomfort.

SUMMARY OF THE INVENTION

Among the objects of the present invention is a provision of an improved traction splint which overcomes the above discussed disadvantageous or undesirable feature, as well as others, of the prior art. Another object of the present invention is the provision of a traction splint which has independently extensible side members such that one of the side members can be extended a distance greater than the other side member to angularly displace the cross member with respect to the side members such that the cross member is positioned closer to the pelvis of the patient to accommodate a femor fracture near the hip of the patient. A further object of the present invention is the provision of a traction splint in which the cross member is formed from a relatively flat flexible plate such that the cross member conformingly flexes to the shape of the patient to abut a large portion of the patient's extremity. These, as well as other features, objects and advantages of the present invention will be in part apparent and in part pointed out hereinafter.

In one embodiment, the present invention is directed to a traction splint for applying traction to an injured limb of a patient. The traction splint includes a pair of spaced, adjustably extensible side members, a traction mechanism coupled to first ends of the side members for exerting a pulling force on the limb, and a cross member traversing second ends of the side members and adapted to abut a portion of the patient. The cross member is pivotally connected to the second ends whereby extending one of the side members more than the other side member angularly displaces the cross member with respect to the side member.

BRIEF DESCRIPTION OF THE DRAWING

The present invention is illustrated by way of example in the figures of the accompanying drawing in which:

FIG. 4 illustrates a plan view of a front support bracket;

FIG. 5 illustrates a side elevational view of the support bracket;

FIG. 6 illustrates a side elevational view, in section, of a locking collar and inner sleeve for telescoping the side members; and FIG. 7 illustrates a top plan view, in section, of a cross member and ischium pad.

Figure 1:
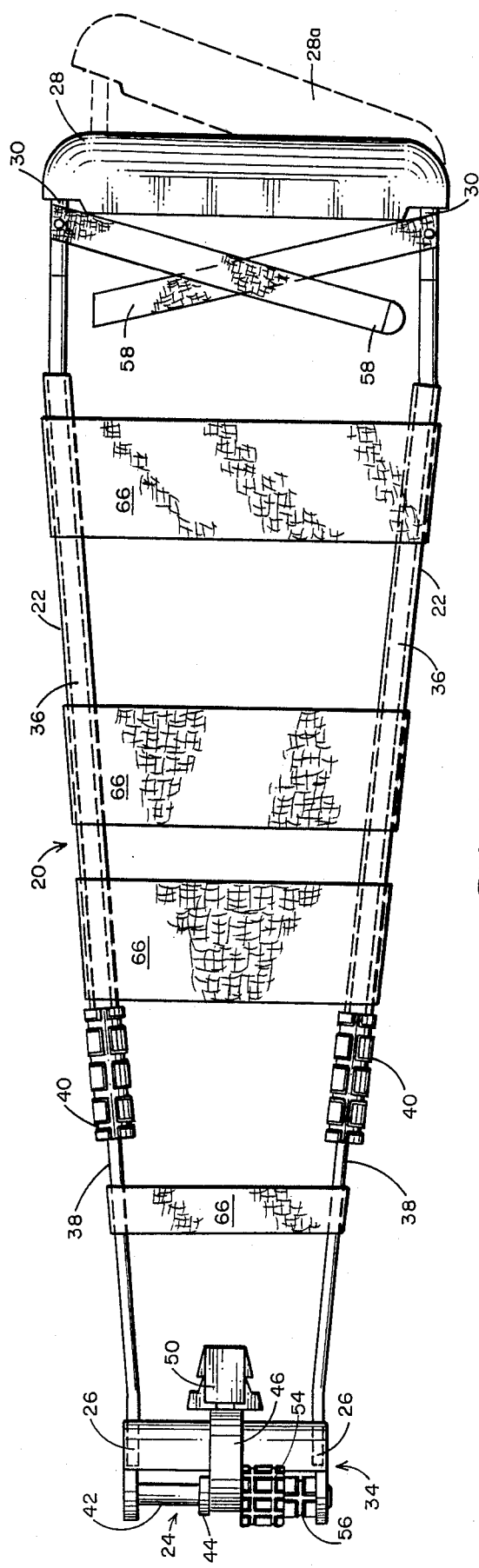
FIG. 1 illustrates a top plan view of a traction splint in accordance with the present invention.

Corresponding reference characters indicate corresponding parts throughout the several views of the drawings. The exemplifications set out here and illustrate the preferred embodiments of the present invention in one form thereof, and such exemplifications are not to be construed as limiting either the scope ofthe invention or the scope of the disclosure thereof in any manner.

DETAILED DESCRIPTION OF THE PREFERRED EMBODIMENTS

With reference to FIGS. 1 through 7 in general, there is illustrated in one form of the invention, a traction splint 20 for applying traction to an injured leg of a patient. The traction splint 20 includes two spaced, adjustably extensible side members 22, a traction mechanism 24 connected to first ends 26 of the side members 22, and a cross member 28 pivotally connected to second ends 30 of the side members 22. Preferably, a front support 32 is pivotally coupled to the first ends 26 of the side members 22 to elevate the distal end 34 of the traction splint 20. The side members 22 can be independently telescoped or extended to angularly displace the cross member 28 such that the cross member 28 is desirably positioned against the body of the patient.

Figure 2:
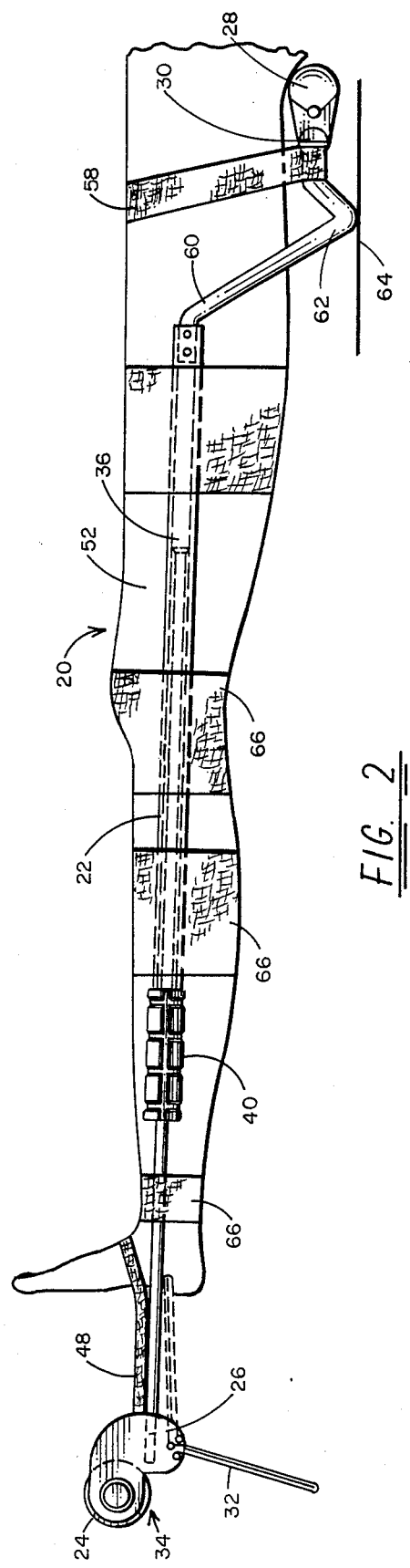
FIG. 2 illustrates a side elevational view of a traction splint in accordance with the present invention.
Figure 3:
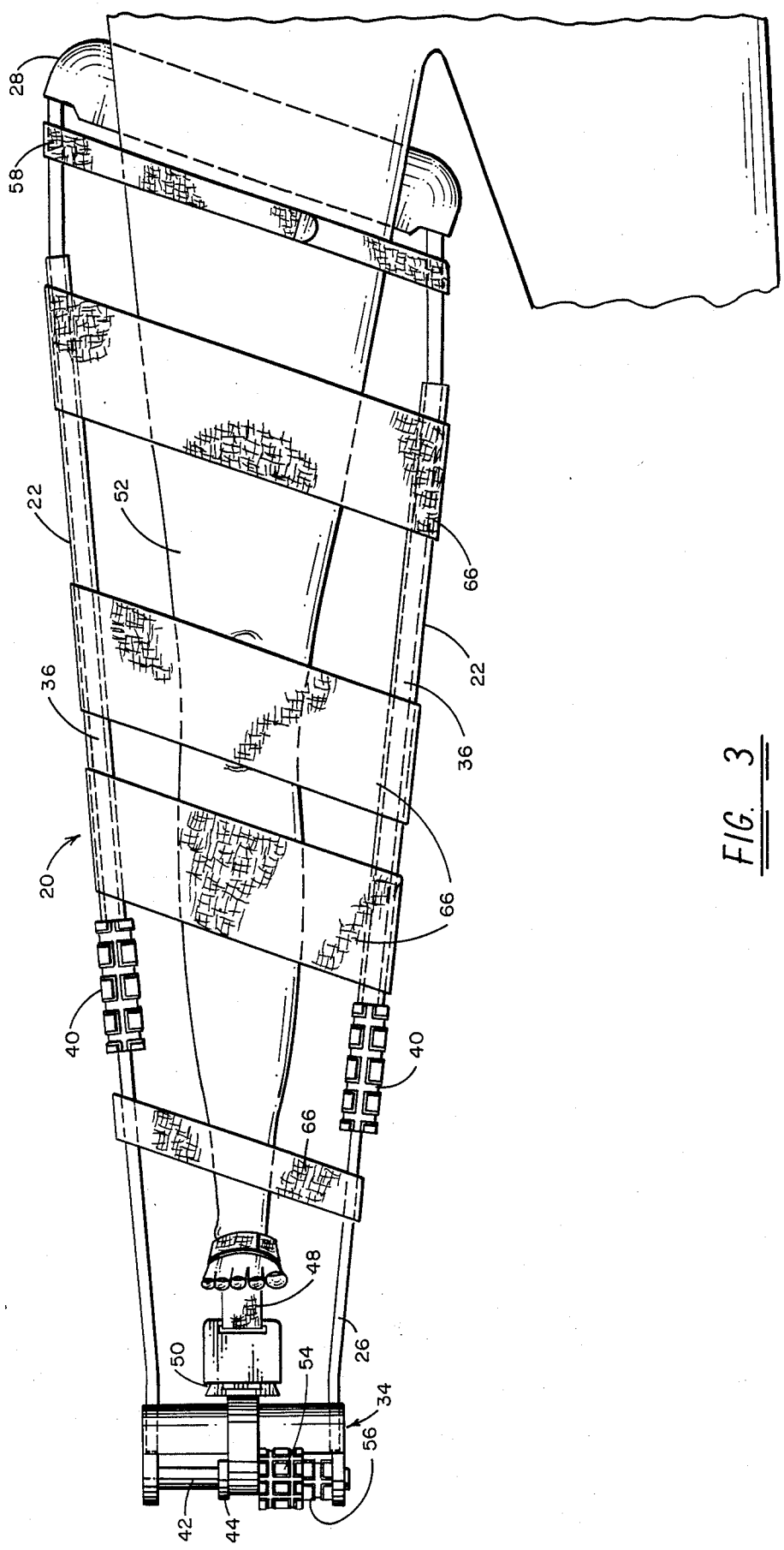
FIG. 3 illustrates a top plan view of a traction splint in accordance with the present invention in which one of the side members is extended a greater length than the other to angularly displace the cross member.

More particular reference is now made to FIGS. 1 through 3 which illustrate, in detail, the traction splint 20. Each side member 22 includes a tubular section 36 coaxially disposed about a rod section 38. The rods 38 adjustably telescope into the corresponding tubular sections 36 to accommodate patients with legs of various lengths. Adjustability of the length of each side member 22 is accomplished by a locking collar 40. The locking collar 40 will be described in greater detail below. By independently telescoping one of the side members 22 a greater length than the other side member 22, the cross member 28 can be angularly displaced as illustrated by the phantom lines 28a. In this manner, an outer portion of the cross member 28 can be positioned closer to the hip of the patient with the inner portion of the cross member 28 still positioned near the groin of the patient. Thus, if a fracture occurs on an upper portion of the femur, greater support of the fracture can be realized, without displacing the fractured bone upward.

The traction mechanism 24 is, preferably, a take up reel, well known in the art, and includes a shaft 42 traversing the first ends 26 of the side members 22. Concentrically disposed about the shaft 42 is a take up spool 44 about which a fabric webbing 46 or the like is wound. An ankle strap 48, dimensioned to wrap around the ankle of the patient, is connected to the fabric webbing 46 by a quick release fastener 50, well known in the art. Traction is applied to the leg 52 of the patient by rotating the spool 44 with respect to the shaft 42 to tension the fabric webbing 46. The spool 44 is rotated by a traction take up knob 54, well known in the art. The traction take up knob 54, maintains the needed traction on the leg 52. A traction release knob 56 is also provided to slowly decrease the traction to the leg by slowly rotating the release knob 56. It is to be understood that tension can also be rapidly reduced by disconnecting the quick release fastener 50 from the ankle strap 48.

A groin support strap 58 is connected to the second end 30 of the side members 222 to support the cross member 28 against the body of the patient. Traction is applied to the leg 52 of the patient between the ankle strap 48 and the groin support strap 58. As shown in FIGS. 2 and 3, the ankle strap 48 is pulling the ankle toward the traction mechanism 24 whereas the groin support strap 58 is pulling the upper portion of the leg 52 toward the cross member 28. Preferably, the second end 30 of each side member 22 comprises a V-shaped tube 60. The apex 62 of the V-shaped tube 60 is adapted for resting on the ground 64 so that the cross member 28 is elevated to push against the body of the patient. Pushing the cross member 28 against the body of the patient further increases the traction to the leg 52 by pushing the body of the patient away from he ankle. Consequently, support to the fracture is increased. Additionally, a plurality of stabilizing straps 66 traverse the two side members 22 for supporting the traction splint 20 against the leg 52 of the patient. Preferably, the stabilizing straps 66 as well as the groin support strap 58 include velcro type mating fasteners, well known in the art, for releasably securing the straps.

Reference is now made to FIGS. 2 and 3 to illustrate attachment of the traction splint to the leg 52 of a patient. Preferably, the cross member 28 rests against the patient's ischium, which is at the lower portion of the pelvis. By positioning the cross member 28 adjacent the ischium, the cross member 28 pushes against the pelvis rather than the femur. If the cross member 28 were positioned against the femur rather than the ischium, a fracture in the upper portion of the femur could not be adequately supported by the traction splint 20. A patient's ischium is positioned slightly above the groin of a patient. Since the side member 22 which is adjacent the groin cannot extend beyond the groin, the side member 22 which is adjacent the outer surface of the leg must be extended a greater length so that the cross member 28 abuts the ischium. This causes the cross member 28 to be angularly displaced with respect to the side members 22. Attachment of the traction splint 20 is accomplished by first independently telescoping each side member 22 to the corresponding length of the patient's leg 52. The traction splint 20 is then slid under the leg of the patient such that the cross member 28 firmly abuts the patient's ischium. The groin strap 58 is then placed around the leg of the patient and the ankle strap 48 is placed around the ankle of the patient. The traction take up knob 54 is then rotated to provide the desired traction to the leg 52. Once the proper traction has been applied, all of the velcro type stabilizing straps 56 are releasably secured around the leg of the patient. Once the traction splint 20 has been applied, the patient can be moved as needed.

Reference is now made to FIGS. 4 and 5 in conjunction with FIG. 2 which illustrate the front support 32. The front support 32 includes a U-shaped member 68 having outwardly pointing ends 70. Two substantially parallel L-shaped members 72 are fixedly secured to the U-shaped member 68 with a first end 74 of one of the L-shaped members extending parallel to one of the outwardly pointing ends 70. Each outwardly pointing end 70 of the U-shaped member rotatably engages with a first aperture 78 through a bracket 76 which is coupled to a corresponding side member 22 of he traction splint 20. With the outwardly pointing ends 70 positioned within the first aperture 78, the front support 32 may be pivoted with respect to the traction splint 20. Preferably, retaining caps or the like are connected to the outwardly pointing ends 70 to prevent the outwardly pointing ends 70 from dislodging with the first apertures 78. The bracket 76 adjacent the extending first end 74 of the L-shaped member 72 is provided with a first locking aperture 80 and a second locking aperture 82. The locking apertures 80 and 82 are dimensioned for engagement with the extending first end 74 of the L-shaped member 72 to lock the front support 32 either in a supporting position or a collapsed position, respectively. With the first end 74 engaged in the first locking aperture 80, the front support 32 is locked in a supporting position substantially normal to the side members 22 and constrained from rotating with respect to the traction splint 20. By squeezing the parallel portions 84 of the L-shaped members 72 together, the first end 74 of the L-shaped member 72 disengages with the first locking aperture 80 and the front support may be rotated to a collapsed position, substantially parallel to the side members 22, and denoted generally by the phantom lines 68a. Rotating the front support 32 into the collapsed position 68a causes the first end 74 to engage with the second locking aperture 82 to lock the front support 32 in the collapsed position. Likewise squeezing the parallel portions 84 of the L-shaped members 74 disengages the first end 74 and the second locking aperture 82. The front support 32 can be rigidly positioned in either a supporting position or a collapsed position.

Reference is now made to FIG. 6 which illustrates how each rod 38 is adjustably extensible with respect to the tubular section 36 of the side member 22. An inner sleeve 84 is secured to the inner surface of the tubular section 36 and extends coaxially from tee end portion of the tubular section 36. The inner sleeve 84 encompasses the rod 38 and is dimensioned to permit the rod 38 to slide with respect to the tubular section 36. The locking collar 40 encompasses the inner sleeve 84 and is coupled to a threaded portion 86 of the inner sleeve 84. The tip end 88 of the inner sleeve 84 is tapered and engages with a tapered inner surface 90 of the locking collar 40. The tapered surface 90 of the locking collar 40 wedges the tip end 88 of the inner sleeve 84 against the rod 38 to lock the rod 38 with respect to the tubular section 36. Rotating the locking collar 40 with respect to the inner sleeve 84 releases the wedging action of the tapered surface 90 against the tip end 88. Once the wedging action is released, the rod 38 may be telescoped with respect to the tubular section 36. Rotating the locking collar 40 in the opposite direction then increases the wedging action and locks the rod with respect to the tubular section 36. Thus, the rod 38 is adjustably telescoped with respect to the tubular section 36.

Reference is now made to FIG. 7 which illustrates the cross member 28. The cross member 28 includes a relatively flat plate 92 and an ischium pad 94 encompassing the flat plate 92. A first clevis 96 and a second clevis 97 are fixed to corresponding opposite ends of the flat plate 92 to pivotally connect the flat plate to the second ends 30 of the side members 22. The plate 92 is formed of a suitably flexible material, such as for instance, aluminum, so that the weight of the patient's body against the flat plate 92 flexes the flat plate 92 to cause it to conform substantially to the shape of the patient's body. Forming the flat plate 92 out of such flexible material increases the area of the patient's body which contacts the cross member 28. Accordingly, the traction forces from the cross member 28 are distributed over a larger area of the patient's body thus minimizing blood constriction and discomfort to the patient's leg. The ischium pad 94 is preferably formed of a resilient material, such a for instance, foam rubber, to further minimize discomfort to the patient. Preferably, the ischium pad 94 is also thinner at the center than at the ends of the pad 94 to form a depression for contouring to the shape of the leg.

While the principles of the invention have now been made clear in an illustrative embodiment, it will become obvious to those skilled in the art, many modifications in structure, arrangement, portions and components used in the practice of the invention and otherwise which are particularly adapted for specific operating requirements without departing from those principles. Accordingly, it is intended that the description be interpreted as illustrative and not in a limiting sense and that the invention be given a scope commensurate with the appended claims.

What is claimed:

1. A traction splint for applying traction to an injured limb of a patient comprising:
    (a) a pair of spaced, continuously adjustably extensible side members, each having a first end and a second end;
    (b) a cross member traversing said second ends of said side members and adapted to abut a portion of the patient, said cross member being pivotally connected to said second ends whereby extending one of said side members more than the other of said side members angularly displaces said cross member with respect to said side members, said cross member comprising a flat plate covered by a resilient pad and formed of a relatively flexible material whereby a force exerted on said cross member from the abutting portion of the patient causes said flat plate to substantially conform to the shape of the abutting portion;
    (c) means coupled to said first ends of said side members for exerting a pulling force on the limb;
    (d) a support assembly pivotally coupled to said first ends of said side members, said support assembly being releasably locatable in an elevated position to raise the patient's limb and releasably locatable in a retracted position, said support assembly comprising:
        (i) first and second brackets attached to corresponding ends of said side members, each bracket having a plurality of apertures substantially aligned transverse to said members with corresponding apertures in the other of the brackets;
        (ii) a U-shaped support member having outwardly extending ends, each of the ends being inserted into one of the plurality of apertures in each of the brackets such that the U-shaped member is pivotable about the ends of the side members;
        (iii) a locking member attached to said support member adjacent one of said ends, said locking member having an end extending into a one of said apertures in an adjacent one of said brackets for preventing rotation of said support member; and
        (iv) said support member being formed of an elastic material whereby opposing sides thereof may be squeezed toward each other to release said locking member to permit rotation of said support member.

2. A traction splint for applying traction to an injured leg of a patient comprising:
    (a) a pair of spaced, adjustably telescoping side members having first ends and second ends;
    (b) a cross member traversing said second ends of said side members and adapted to abut a portion of the patient adjacent the ischium of the patient, said cross member being pivotally connected to said second ends whereby telescoping one of said side members more than the other of said side members angularly displaces said cross member with respect to said side members, said cross member comprising a flat plate covered by a resilient pad and formed of a relatively flexible material whereby a force exerted on said cross member from the abutting portion of the patient causes said flat plate to substantially conform to the shape of the abutting portion;
    (c) means coupled to said first ends of said side members for exerting a pulling force on the leg;
    (d) a plurality of Velcro type stabilizing straps traversing said side members and adapted to constrain the leg with respect to said side members;
    (e) a support assembly pivotally coupled to said first ends of said side members for supporting the leg above any surface on which the patient is positioned;
(f) a support assembly pivotally coupled to said first ends of said side members, said support assembly being releasably locatable in an elevated position to raise the patient's limb and releasably locatable in a retracted position, said support assembly comprising:
  (i) first and second brackets attached to corresponding ends of said side members, each bracket having a plurality of apertures substantially aligned transverse to said members with corresponding apertures in the other of the brackets;
  (ii) a U-shaped support member having outwardly extending ends, each of the ends being inserted into one of the plurality of apertures in each of the brackets such that the U-shaped member is pivotable about the ends of the side members;
  (iii) a locking member attached to said support member adjacent one of said ends, said locking member having an end extending into a one of said apertures in an adjacent one of said brackets for preventing rotation of said support member; and
  (iv) said support member being formed of an elastic material whereby opposing sides thereof may be squeezed toward each other to release said locking member to permit rotation of said support member.

* * * * *